(12) United States Patent
Stokes et al.

(10) Patent No.: US 8,632,964 B2
(45) Date of Patent: Jan. 21, 2014

(54) DETECTION SYSTEM

(75) Inventors: Robert Stokes, Glasgow (GB); Duncan Graham, Edinburgh (GB)

(73) Assignee: University of Strathclyde, Glasgow (GB)

( * ) Notice: Subject to any disclaimer, the term of this patent is extended or adjusted under 35 U.S.C. 154(b) by 930 days.

(21) Appl. No.: 12/475,141

(22) Filed: May 29, 2009

(65) Prior Publication Data

US 2010/0028908 A1     Feb. 4, 2010

Related U.S. Application Data

(60) Provisional application No. 61/057,558, filed on May 30, 2008.

(51) Int. Cl.
*C12Q 1/00*     (2006.01)

(52) U.S. Cl.
USPC .............................................................. 435/4

(58) Field of Classification Search
None
See application file for complete search history.

(56) References Cited

U.S. PATENT DOCUMENTS

| | | | |
|---|---|---|---|
| 5,721,102 A * | 2/1998 | Vo-Dinh | 435/6.12 |
| 6,174,677 B1 * | 1/2001 | Vo-Dinh | 435/6.11 |
| 6,635,311 B1 | 10/2003 | Mirkin et al. | |
| 6,827,979 B2 | 12/2004 | Mirkin et al. | |
| 7,195,872 B2 * | 3/2007 | Agrawal et al. | 435/287.2 |
| 7,474,397 B2 * | 1/2009 | Wang et al. | 356/301 |
| 2003/0059820 A1 * | 3/2003 | Vo-Dinh | 435/6 |
| 2003/0068446 A1 | 4/2003 | Mirkin et al. | |
| 2007/0087172 A1 * | 4/2007 | Mirkin et al. | 428/195.1 |
| 2010/0099579 A1 * | 4/2010 | Chilkoti | 506/16 |

FOREIGN PATENT DOCUMENTS

WO    WO 03/048314 A2    6/2003

* cited by examiner

*Primary Examiner* — Ann Lam
(74) *Attorney, Agent, or Firm* — Alston & Bird LLP

(57) ABSTRACT

The present invention relates to methods of making nanoarrays for use in detecting species formed on the surface of the array using SE(R)RS. The methods can involve nanolithographic printing of a compound by dip pen nanolithographic printing. A SE(R)RS substrate can be used for the array and which can be selected from surfaces roughened by the oxidation-reduction cycle (ORC), island films, colloidal nanoparticles and surface-confined nanostructures. A coating or intermediate layer, such as a layer formed of nitrocellulose, can be provided between the compound and the SE(R)RS substrate. There are also provided arrays themselves and methods of using such arrays.

13 Claims, 3 Drawing Sheets

DETECTION SYSTEM

CROSS REFERENCE TO RELATED APPLICATIONS

Figure 1:
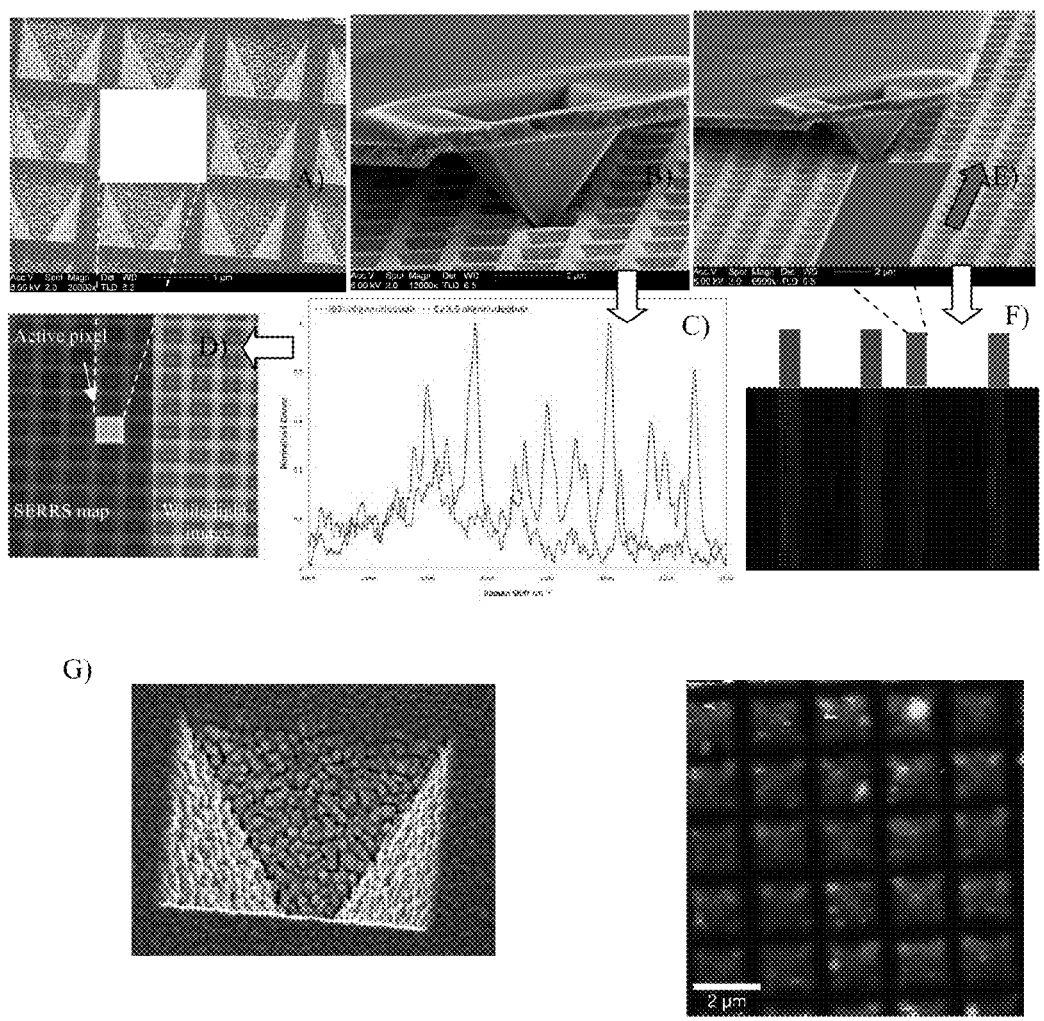

This applications claims benefit of U.S. Provisional Application No. 61/057,558, filed May 30, 2008, which is hereby incorporated herein in its entirety by reference.

FIELD OF THE INVENTION

The present invention relates to methods of making nanoarrays using dip pen nanolithography for use in detecting species formed on the surface of the array using SE(R)RS. There are also provided arrays themselves and methods of using such arrays.

BACKGROUND OF THE INVENTION

This invention spans the fields of nanotechnology and optical science. More particularly, it concerns the fields of nanolithography especially Dip-Pen Nanolithography (DPN) and the optical technique of surface enhanced Raman scattering (SERS). Dip-Pen Nanolithography (DPN), is a versatile technique in which a scanning probe microscope tip can be used to deliver a material ("ink") to a surface via a water meniscus. DPN allows controlled deposition of suitable materials conventionally onto a flat substrate, with the size of the feature being written related to the complex interaction between the tip, ink, meniscus and surface. Further development of the technique has allowed Mirkin and co-workers to report direct and indirect writing of biological materials onto suitable surfaces to form highly structured arrays. DPN lithography can be carried out in both dot and line modes. Dot patterning involves the tip being moved vertically into contact by a Z piezoelectric motor action and the tip is lifted off between contact points. In line writing mode the tip staying in contact with the surface as it is moved by X and Y piezoelectric motors. Because the feature sizes produced by DPN are so small, detection of biological interactions is often achieved by atomic force microscopy (AFM: lateral force or tapping mode) or, as is most common in the case of DPN-directed DNA arrays, a fluorescence readout method is used.

Imaging and detection of single monolayers of a material or analyte at a flat surface is difficult. In the case of analysis by lateral force microscopy (LFM), imaging can only be effectively carried out where the surface is sufficiently flat to provide high contrast between areas containing the monolayer. Likewise in contact or tapping modes the imaging and detection quality is limited by the roughness of the underlying surface.

SERS is a highly sensitive spectroscopic technique that has been used in an increasing number of applications in biodiagnostics including gene probes, and DNA detection. The technique is flexible and with controlled chemistry can be performed using longer biologically suitable wavelengths of excitation ($\lambda_{ex}$) in solution, or on nanostructured plasmonic gold surfaces. In surface enhanced Raman scattering the Raman signal from the analyte is enhanced dramatically by the proximity of the analyte to areas of high electric field. In SERS systems using nanoparticles or nanomaterials the field is generated on features of particular curvature or points where the oscillating electric field strength is strongest. A number of effective SERS substrates have been reported in recent years, including those fabricated by nanosphere lithography (NSL), silver metal island films and nanostructured gold surfaces. In SERS substrates the surface topography is always non-flat and the enhancement derives from areas of strong electric field gradient such as at sharp points (as in NSL) or standing waves set up in wells or cavities.

In addition to SERS, surface enhanced resonance Raman scattering (SERRS) potentially offers a number of significant advantages over other forms of detection such as fluorescence detection. When considering the simultaneous detection of multiple targets, it is significant to note that, in SERRS, a large proportion of the overall enhancement derives from the additional 'resonance' with the molecular chromophore. The resonance Raman spectrum from reporter dyes typically comprise fewer strong lines than would normally be expected from a larger molecule, as only certain vibronic states are probed using single wavelengths of excitation. This is a major advantage of the technique, when applied in a real assay, as a number of characteristic bands within each dye class are enhanced to a greater extent than other materials in the matrix. The characteristic narrow SERRS lines (~0.5 nm width) have the potential to form the basis of an highly effective multiplexed analysis from a single excitation source. A further advantage of SERRS is that the excitation wavelength can be selected anywhere in the optical range and wavelength selectivity can be observed using some combinations of dye reporters.

SUMMARY OF THE INVENTION

The present invention is based on observations by the present inventors that it is possible to deposit/write molecules, such as DNA oligonucleotides directly onto a SE(R) RS sensitive substrate, using the technique of dip pen nanolithography (DPN) and to detect biomolecular complexes formed between the substrate bound molecule and a target analyte using SE(R)RS.

Thus, in a first aspect, there is provided a method of making a nanoarray for use in SE(R)RS detection comprising:

patterning a compound on a suitable SE(R)RS active substrate by nanolithographic printing especially dip pen nanolithography, for form a pattern.

The technique of dip pen nanolithographic printing is well known in the art, further details can be found in U.S. Pat. No. 6,635,311, U.S. Pat. No. 6,827,979, WO03/048314 and US2003/0068446, to which the skilled reader is directed and the disclosures of which are hereby incorporated by way of reference.

It is to be appreciated that SE(R)RS refers to SERS (surface enhanced Raman scattering) and SERRS (surface enhanced resonance Raman spectroscopy), with SERRS being preferred. This should not however be construed as limiting, as other scattering or wave-resonance detection techniques including Raleigh scattering and surface Plasmon resonance could also be employed.

A disadvantage of conventional uses of DPN is that although the writing aspect allows extremely small areas/lines to be deposited, this itself can cause reading problems, and reading may have to be carried out using an atomic force microscope (AFM) or the like. Such apparatus are extremely expensive and not suited to routine assay protocols. Advantageously, the present invention which using DPN to carry out the writing aspect, the reading aspect can more easily conducted using more simple and readily available optical readers. Thus, the arrays of the present invention may be created using DPN techniques, but the reading can be carried out easily by SE(R)RS analysis.

Many suitable SE(R)RS substrates are known in the art and are generally roughened surfaces, especially metal surfaces. These include surfaces roughened by the oxidation-reduction cycle (ORC), island films, colloidal nanoparticles and surface-confined nanostructures (see Hanes et al., Analytical Chemistry, Sep. 1, 2005, p 338-346). One particularly preferred substrate is Klarite® (D3 Technologies, Glasgow, Scotland). Klarite substrates feature a systematically designed nanometer scale patterning of a silicon surface that is coated in gold. Made of regular arrangements of holes, the surface patterns form photonic crystals that control the surface plasmons that govern the Raman enhancement process.

The present inventors have found that it is possible to write directly, using DPBN, into the wells of the Klarite® material. Indeed, this knowledge shows that it is possible to accurately write onto specific locations and features of Klarite and other SER(R)RS substrates, e.g., corners, junctions, peaks, etc., in order to control or maximise SE(R)RS signal intensity/enhancement.

Another advantage of the present invention is the ability to write features which are closer together than the diffraction limit. Thus, it is possible to write features using DPN, at a density which would result in an overlap of spectral signals, but given the unique and specific spectral signatures, it is possible to separate the information and identify the signals.

The arrays of the present invention can be extremely small, for example 100 nm×100 nm, but any size of array can be formed, with the written features being as small as down to about 14 nm and having spacings of 14 nm. The features may be in the form of dots on the surface or lines. Where the features are in the form of lines, they may be read using SE(R)RS line mapping techniques known in the art.

As well as writing directly onto the SE(R)RS active surface, the present inventors have observed that form some SE(R)RS active surfaces it is possible to provide a coating or intermediate layer between the molecule being bound and the SE(R)RS active surface. Detection of the SE(R)RS signal is still possible and the coating or intermediate layer can assist or improve the binding of the particular molecule to the SE(R)RS active surface. For example, the inventors have provided a layer of nitrocellulose on a SE(R)RS active surface, in order to facilitate binding of proteins in an active configuration.

In one embodiment, the array is formed such that the patterned features are written onto the SE(R)RS active substrate, such that in use, the reading device, for example, laser spot focus point, is not directly over the patterned feature(s). This utilises the fact that the surface plasmons are capable of limited travel over the SE(R)RS surface and as such can be detected at a location close to but not directly on the laser spot focus point. Not only does this reduce the possibility of photobleaching and localised heating damage which may be caused by the laser, but also permit the laser spot to focus at one particular point and take readings from various point around the periphery of the focus point.

As described in further detail herein, the formation of a complex formed between the substrate bound molecule and its binding partner can easily be carried out using appropriate optical devices known in the art, which scan the surface of the substrate. In one embodiment, the SE(R)RS scanning/reading can be coupled with reflectivity reading. In this way a fast reflectivity scan can be conducted to identify areas on the area which display altered reflectivity, which can thereafter be scanned using SE(R)RS techniques.

In a further aspect there is provided a method of detecting the formation of a surface bound species formed between two biological components where one of the biological components has been deposited onto the surface of a SE(R)RS active substrate using DPN, the method comprising the step of: detecting whether or not said surface bound species has formed by way of using SE(R)RS analysis.

Typically said one of the biological components is deposited on a substrate as a component of a nanoarray comprising a plurality of different deposited components. Generally, a sample potentially containing a binding partner for said substrate bound biological component will be contacted with the substrate in order to allow any complex formation to occur.

Examples of analytes which may be detected include, nucleic acids, nucleic acid analogues, proteins, peptides, enzymes, prions, antibodies, aldehydes, amines, explosives, drugs of abuse, therapeutic agents, metabolites and environmental pollutants. This is not however exhaustive, as any suitable analyte may be detected. The analyte may be obtained from a sample and the sample may be any suitable preparation in which the target analyte is likely to be found. However, conveniently the sample may be in a fluid, or in solution or transferred to a solution before contacting with the substrate.

For effective SE(R)RS analysis, a chromophore of a suitable wavelength to be in resonance with the laser chosen, must be present in the analyte or a chromophore must be created by derivatisation of the analyte before analysis. Moreover in either case effective adsorption to the surface must be achieved. In this invention, this is generally achieved by forming, for example, a complex between the target analyte and the substrate bound molecule. Typical complexes include protein/protein, nucleic acid/nucleic acid, protein/nucleic acid and protein/antibody. Any reference herein to the term protein is understood to extend to protein fragments, peptides and the like and is not therefore size limiting. The same is true for antibodies and nucleic acid molecules.

Adhering the "capture" molecule with the SE(R)RS active surface will typically be by chemi-sorption of the molecule onto the surface, or by chemical bonding (covalent, chelating, etc.) of the molecule with either the surface or a coating on the surface, either directly or through a linking group. The association will usually be via suitable functional groups on the molecule, such as charged polar groups (eg. $NH_3^+$ or $CO_2^-$), attracted to the surface or surface coating. Clearly, the type of association will depend on the nature of the surface and the label in any given case; different functional groups will be attracted to a positively-charged surface, for instance, as to a negatively-charged one.

Suitable groups by which the molecule may be bound to the active surface include complexing groups such as nitrogen, oxygen, sulphur and phosphorous donors; chelating groups; bridging ligands and polymer forming ligands. Specific details of preferred methods of adhering a molecule with a SE(R)RS active substrate are described in WO97/05280.

The method for obtaining the SERRS spectrum, once the analyte complexes, binds or otherwise adheres to the molecule which has been adhered to the substrate, may be conventional. By way of example, however, the following might apply to the spectroscopic measurements:

Typically, the methods of the invention will be carried out using incident light from a laser, having a frequency in the visible spectrum ie. ~380 nm-850 nm, particularly between 400 nm-650 nm (the exact frequency chosen will generally depend on the chromophore used in each case—frequencies in the red area of the visible spectrum tend, on the whole, to give rise to better surface enhancement effects but the fourth power of Raman means that blue is better and many chromophore lie in the green region giving maximum resonance enhancement there. However, it is possible to envisage situations in which other frequencies, for instance in the ultraviolet (ie. 200 nm-400 nm) or the near-infrared ranges (700 nm-1100 nm), might be used. Thus, SE(R)RS detection may be conducted between about 300 nm-1100 nm.

The selection and, if necessary, tuning of an appropriate light source, with an appropriate frequency and power, will be well within the capabilities of one of ordinary skill in the art, particularly on referring to the available SE(R)RS literature. To achieve highly sensitive detection, using SE(R)RS, a coherent light source is needed with a frequency at or close to the absorption maximum for the chromophore or that of the surface plasmons. If lower sensitivities are required, the light source need not be coherent or of high intensity and so lamps may be used in combination with a monochromator grating or prism to select an appropriate excitation frequency; here, there is no need to operate at the resonant frequency of the chromophore or the plasmons.

The light can be conducted from the source to the active surface by reflection in mirrors and can be focussed to give a higher light flux by passing through lenses. A suitable apparatus for SE(R)RS analyses is a microscope with signal detection at 180 degrees to the excitation beam. A fluorescence microscope with confocal optics is also appropriate. The use of microscope optics permits the very small deposits of an array device to be analysed.

Several devices are suitable for collecting SE(R)RS signals, including wavelength selective mirrors, holographic optical elements for scattered light detection and fibre-optic waveguides. The intensity of a SE(R)RS signal can be measured for example using a charge coupled device (CCD), a silicon photodiode, or photomultiplier tubes arranged either singly or in series for cascade amplification of the signal. Photon counting electronics can be used for sensitive detection. The choice of detector will largely depend on the sensitivity of detection required to carry out a particular assay.

Note that the methods of the invention may involve either obtaining a full SERRS spectrum across a range of wavelengths, or selecting a peak and scanning only at the wavelength of that peak (ie. Raman "imaging").

Apparatus for obtaining and/or analysing a SE(R)RS spectrum will almost certainly include some form of data processor such as a computer.

Raman signals consist of a series of discrete spectral lines of varying intensity. The frequencies and the relative intensities of the lines are specific to the derivatised analyte being detected and the Raman signal is therefore a "fingerprint" of the derivatised analyte. If a SE(R)RS analyser is being used selectively to detect one analyte out of a mixture then it will be necessary to detect the entire "fingerprint" spectrum for identification purposes. However if the analyser is being used to quantitate the detection of one or several analytes, each of which has a unique spectral line, then it will only be necessary to detect signal intensity at a chosen spectral line frequency or frequencies, or to detect all Raman scattering using a filter to exclude Rayleigh scattering.

Once the SE(R)RS signal has been captured by an appropriate detector, its frequency and intensity data will typically be passed to a computer for analysis. Either the fingerprint Raman spectrum will be compared to reference spectra for identification of the detected Raman active compound or the signal intensity at the measured frequencies will be used to calculate the amount of Raman active compound detected.

A commercial SE(R)RS analyser of use in carrying out the invention would be expected to consist of the following components: a laser light source, the appropriate optics for carrying the light to the SE(R)RS active surface, a stage for mounting the array device for analysis, optics for receiving the Raman signal, a detector for converting the Raman signal into a series of intensities at certain wavelengths and a data processor for interpreting the wavelength/intensity data and providing an analytical output.

One application particularly suited to detection using the method and/or device according to the present invention is the detection of extremely small amounts of DNA for the analysis of, for example, single nucleotide polymorphisms (SNPs).

The basic approach makes use of the fact that SE(R)RS can identify different chromophores based on molecular structure. Thus, a label can be generated in situ by the reaction of a SE(R)RS activating agent and a specific tag attached to the molecule of interest. However, the tagged species does not produce any SE(R)RS on its own, and only therefore produces a SE(R)RS signal when in combination with the SERRS activating agent (see EP1440317 for further description of this).

The present invention will now be further described by way of example and with reference to the following figures which show:

FIG. 1: SEM micrographs of (A) Klarite™ nanostructured gold surface, (B) AFM tip interaction with surface. (C) SERS spectra obtained from ROX and Cy3.5™ dye-labelled oligonucleotide sequences written (1×1 μm area) into single well [1×1 s, $\lambda_{ex}$=632.8 nm, 0.6 μW]. (D) SERRS map of single Cy3.5 oligonucleotide pixel (false colour map over white light image), showing signal (at 1280 cm$^{-1}$) from only one pixel (1.3 μm/map pixel). (E) Representation of DPN line writing (F) Dual target line mapping image recorded from orthogonally broad DPN lines drawn onto Klarite™. Image consist of overlaid false colour maps with the intensity based on 1370 cm$^{-1}$ (Cy3.5™, Purple) and 1600 cm$^{-1}$ (Cy5™, blue) integrated peak area to base line G) Detail of a single surface SERS well feature. H) Example scanning confocal Raman image of an area modified by the thioctic acid surface chemistry. Stronger Red colouration indicates higher intensity of Cy3.5™ labelled sequence. The SERS signal only originates from sample wells. In particular, the strongest SERS signals originate from areas of high electric field (hot spots) at the centre and the junctions between facets of the inverted pyramid. Image recorded in collaboration with Thomas Dienig (WITec, Ulm Germany).

Figure 2:
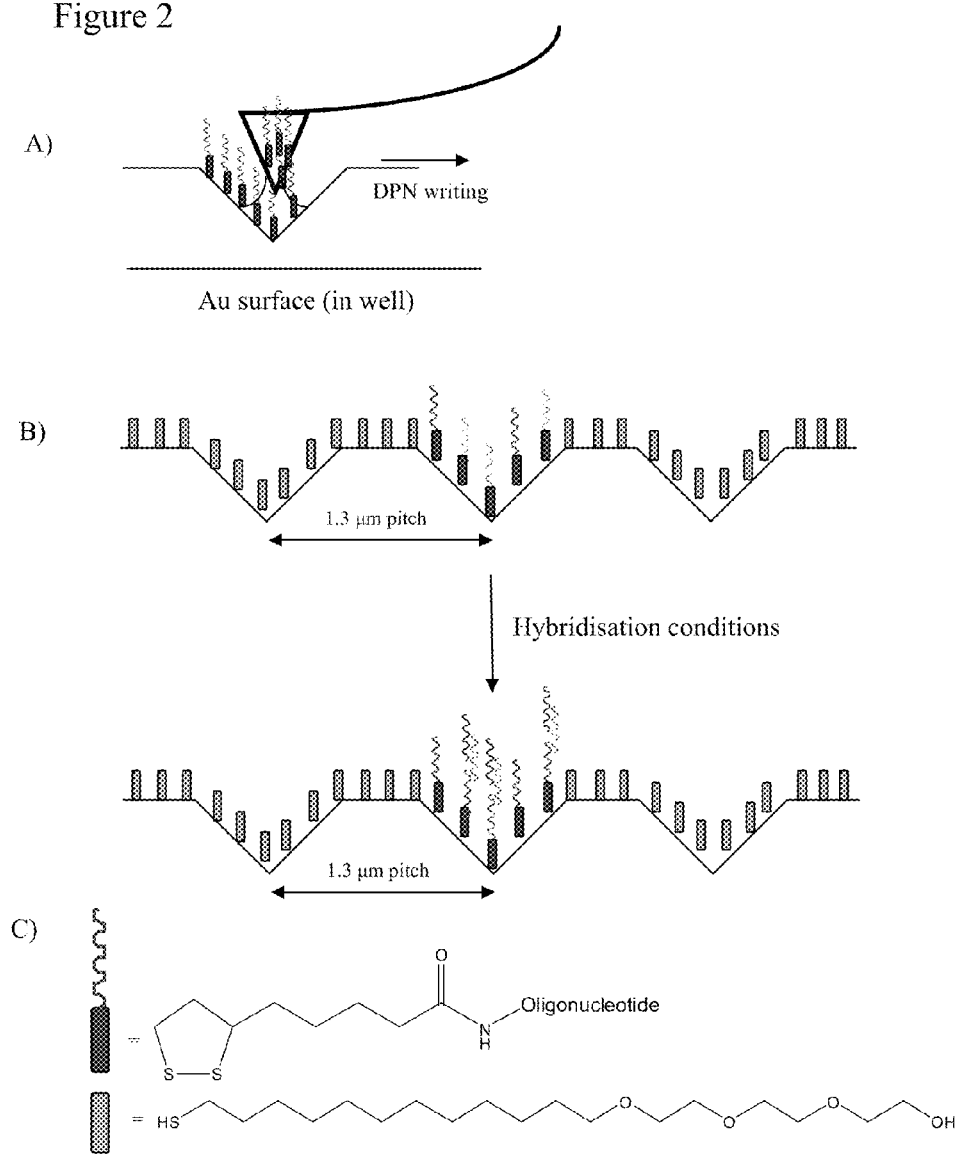

FIG. 2: Example schematic of typical DPN deposition and surface chemistry: A) DPN capture strand direct-write via disulfide-modified oligonucleotide deposition, B) Passivation with triethylene glycol mono-11-mercaptoundecyl ether is followed by "sandwich" hybridisation with target (green) and dye-labelled probe (blue), C) Representation of disulfide-modified oligonucleotide and PEG-passivator.

Figure 3:
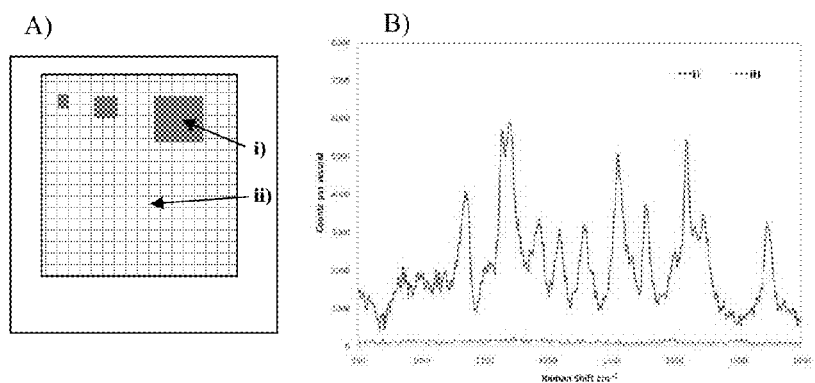

FIG. 3: A) Schematic of typical DNA hybridisation experiment. i) SERS active capture areas: e.g. 1-3 microwells². Where oligonucleotide capture strand has been written by DPN and exposed to target and dye labelled complement. ii) "Blank" areas: where the surface has been passified using triethylene glycol mono-11-mercaptoundecyl ether and subsequently exposed to identical hybridisation materials and conditions. B) SERS spectra (4×4 microwell) from active area after hybridisation of disease target probe and dye labelled complement oligonucleotide (Cy5™). [1×1 s, $\lambda_{ex}$=632.8 nm, 0.6 μW, leveled and set to zero].

Figure 4:
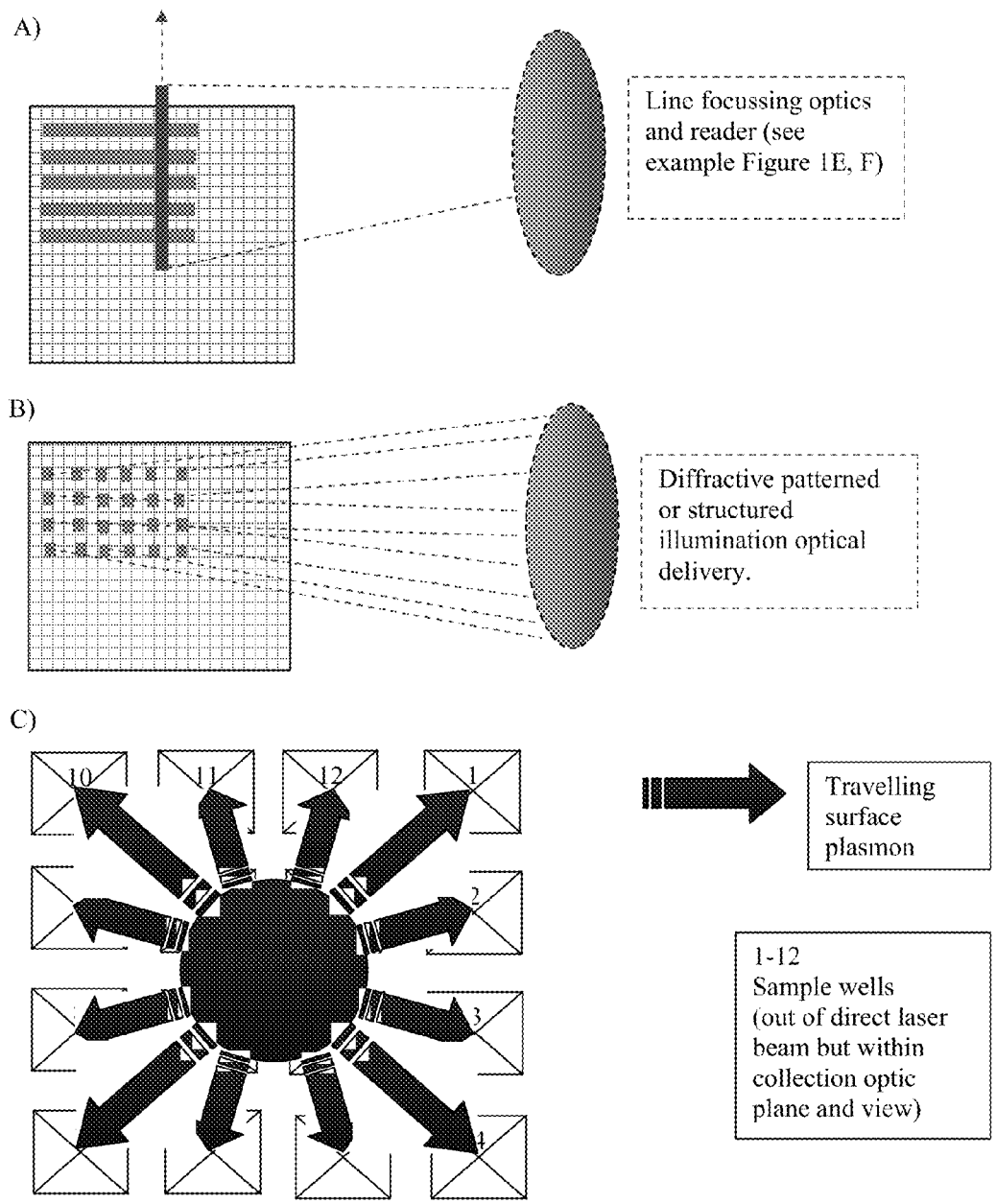

FIG. 4: DPN directed arrangement of capture or analyte material on sub- or close to diffraction limit dimensions. A) Line patterning with line scanning optics, B) Nanopattern arrangement with structured or patterned light illumination, C) Example of travelling surface plasmon arrangement whereby the sample may be placed precisely a point very close to but not exactly on to the laser spot focus point. This reduces the possibility of photobleaching and localised heating damage.

DETAILED DESCRIPTION OF THE INVENTION

The inventors show that DPN can be performed accurately in single plasmonic microwells. Furthermore, they have shown that the SE(R)RS readout of these single microwell array dots can be read in isolation by fast line scanning (see FIGS. 1B, C and D) or excited remotely from a point close to but not exactly on the collection point (when collecting in a confocal or semi-confocal set-up.)

The inventors also show that it is possible to write lines of material onto non-flat nanostructured surfaces using suitable cantilevers and methods.

1) DPN SERS Array Fabrication:

The lithography method differs according to the type of SE(R)RS surface used. For example, nanostructured gold surfaces of the type detailed by Perney and co-workers[13] (and shown in FIG. 1A) rely on a inverse pyramid structure with topography and spatial features on the microscale (~1.3 µm pitch). This design feature is necessary to create surface plasmon resonances and areas of strong electric field (necessary for SE(R)RS enhancement) at the surface. The surface topography means that it is very difficult to print evenly into this small 3D domain, by conventional methods. Furthermore, each surface "well" also contains a large amount of roughened gold. Points of curvature or features suitable for enhancing the local electric field, further increase the enhancement effect of the SE(R)RS (or fluorescence signals). These (often delicate) sub wavelength sized features are integral to almost all SE(R)RS substrates. Therefore, any contact lithography method cannot deploy a large force to critical areas, without damage occurring. Too great a force acting on the surface damages the gold surface, causing scratches and damaging the delicate nanostructured interior of the well, ultimately resulting in both a reduction in both SE(R)RS enchantment and the reproducibility of the signals arising from each feature. This is important as a scratch or area where gold particles are brought together in close proximity may result in a significant increase in local SE(R)RS intensity, whereas an area with little or less roughened gold will result in a decrease in over SE(R)RS enhancement. Dot patterning results in the least potential for sample damage as the tip is lifted between contact points. However, in order to achieve a consistent and strong signal for many SE(R)RS surfaces it is often necessary to raster the tip within the sample area in order to deliver capture or analyte material to either a) the whole active area of the feature, or b) specific areas where the electric field is strongest. This method, along with line patterning across features requires contact to be maintained across areas where significant Z travel is required (such as from centre of one well to another in the example shown in FIG. 1B).

Specifically, it is the combination of the spring constant [k] of the cantilever and the aspect ratio of the tip that is critical in achieving effective SE(R)RS patterning in many types of SE(R)RS surface. For example, using standard aspect ratio A type pyramid AFM/DPN probes (Nanoink, Skokie, Ill.) it was found that the "A-frame" end with a spring constant [k] of 0.1 N/m was not suitable for DPN lithography on this surface. Conversely effective lithography in both line/raster and dot modes can be achieved by the use of a lower spring constant cantilever (e.g. 0.041 N/m). This is because the force that is applied is smaller when the tip approaches the non-flat regions of the feature and the cantilever is forced to bend. If the aspect (height to width) ratio of the tip is smaller than that of the 3D surface feature that is being written, then the sides of the tip will cause damage to the sides of the feature as the AFM tries to stay in contact. Furthermore, the gains or values in the feedback system to keep the tip in contact cannot be set too high when patterning at higher tip speeds in 3D SE(R)RS structures. This is due to the fact that the tip will not respond quickly enough to the large change in Z height as it approaches microscale features (such as the side walls of each well in the example in FIG. 1). When the tip contacts the side of the well in this way without the lithography device (e.g. the AFM or similar device) lifting off quickly enough then sample damage will occur to the roughened gold as a disproportionally high force is applied by the X and Y motors via the side of the tip to the feature wall.

DPN SE(R)RS arrays can also be patterned using tips that have a 'dog-leg' or bend. These allow patterning of some surface single faced features, but are not suitable in cases where the feature contains 2 or more facets, unless rotation or realignment is used.

2) SE(R)RS "Reading": The Relationship Between Surface Features, DPN Features and the Efficiency of the Over SE(R)RS System.

DPN or similar contact lithography can be used to create patterns on non-flat surfaces suitable for SE(R)RS. If the pattern is written in lines or dotted (using the methods described above), then the overall efficiency of the SE(R)RS array can be optimised. For example, using suitable tip speed, aspect ratio and k (as described above), to pattern continuous lines allows patterns to be created that are highly suited to a line scanning Raman mapping approach (FIG. 4A). Raman line scanning (e.g. Renishaw Streamline system) utilises a line defocused beam to raster across the area to be scanned. A number of spectra are simultaneously recorded from the area under the beam across a large area of the CCD. DPN line writing onto SE(R)RS substrates creates a new type of biosensor array. By scanning across the written lines orthogonally a highly efficient read-out system is generated. The line focussing is particularly suited to DPN generated arrays as this type of system effectively sacrifices laser power density (by line focussing) and increases effective exposure time (by line scanning) to compensate. Plasmonic SE(R)RS surfaces of this type primarily contain only monolayer or sub-monolayer amounts of material to be detected, and this is key to the highly sensitive measurements that can be achieved using them. Therefore, only low power densities (order of ~$10^{-4}$ $W \cdot cm^{-2}$) are suitable for these arrays, as excess power will cause damage to both the analyte/capture material (either by photo-bleaching/photo-dissociation or localised heating-thermal degradation). Equivalent point mapping/confocal scanning requires the use of neutral density filters (NDF) to attenuate the laser power to between 1 to 0.01% of the original power. As the line scanning method utilising only low surface power density, the combined DPN-SE(R)RS-line scanning array technique is more that 100 times efficient in terms of laser power than both point mapping or scanning confocal Raman measurements. The inventors have shown this experimentally where the use of efficient surface modification chemistry (FIG. 2) produces highly efficient and even SE(R)RS signals from the surface features. Using these DPN-directed modification methods it is possible to run a line scanning system at the maximum speed permissible by the stage and CCD. Depending on the optics used the line scanning system can read 30-60 times more spectra than the equivalent point mapping system. A further advantage of this combined method is the fact sample alignment is minimised. Information density in this arrangement can be very high (and utilise sub-wavelength features due to the information rich spectra of SE(R)RS as the width of the lines can be very small (currently as small as 14 nm), however an advantage of the DPN/nanoprobe writing system is that the lines can be many orders of magnitude in length. Therefore, as long as the sample is arranged roughly in an orthogonal manner to the laser line spatially then the system will read the sample in a manner similar to a barcode.

It is possible to isolate the SE(R)RS signal from a single well (FIG. 1 above). It is also possible to collect the scattered light from a point offset from the major laser focus point. This is due to the fact that the surface plasmons are able to travel several micrometers on gold surfaces (depending on wavelength and the composition of the substrate). Therefore, it is possible to use DPN to deposit features sufficiently close to a central spot (under which the region is effectively sacrificed) in order to gain enhancement and SE(R)RS from the beam in the surrounding wells. Collecting at points either spatially offset (or by blocking the major focus point through use of optics) allows the localised heating and photodegradation of the samples to be reduced whilst simultaneously taking advantage of the SE(R)RS (FIG. 4C). Although the SE(R)RS is weaker at point spatially offset from the laser focus point, it is still strong enough to provide significant signals for detection without the need for complicated or specialist optics. Use of a masked or "hollow" laser spot can be used to create the inverse of this set-up maximising sensitivity (but sacrificing the outer surface features in order to enhance the scattering from the central feature/well. In either case, DPN on the 3D surfaces provides the versatility to fabricate such array types.

The inventors have also proven that it is possible to use the very narrow SE(R)RS lines in a spectrum to image directly using a narrow bandpass filter.

3) Surface Modification: To Increase Activity and Functionality:

DPN can be used to either modify the array surface in order to achieve additional functionality or in order to create enhanced or optimised SE(R)RS conditions. Three examples are detailed below:

3-A: DPN Writing onto Non-Metal SE(R)RS Active Surfaces.

Conventionally, SE(R)RS arises from the molecules very close to the surface feature under examination. This is due to the fact that the electric field decays with distance away from the surface. However, some SE(R)RS substrates (such as that shown in FIG. 1) possess micro and nanostructures to allow considerable electric field strength to be generated in areas that are a significant distance above the surface. Therefore, this allows some SE(R)RS substrates to function despite the fact that there is an additional layer between the metal surface and the analyte. This material can either be a capture material (such as the DNA and thiol chemistry shown in FIGS. 2 and 3) or a generic material that increases the effectiveness of the DPN writing for some materials. For example: on gold surfaces thiol chemistry is most often used. However, it is necessary in some cases (especially using proteins) that an additional molecular layer is placed between the metal surface and the analyte, in order to provide a "molecular mattress" to cushion the interaction between proteins and the gold surface. Without this layer the tertiary structure of the protein (and the effectiveness of the array) is often lost. Although many types of coating can be created by spin-coating or evaporation, it is possible to use DPN to pre-modify the SE(R)RS surface. This has and advantage in that the DPN can write directly and exclusively into the features of interest, meaning that less material is wasted coating surrounding areas. This also has the effect that surface plasmons are free to propagate across areas of the surface that are not directly involved in scattering (SE(R)RS). This increases the overall efficiency of the array. A large number of materials that can be used to pre-modify surfaces including: a) Thiol-alkylchain-poly-ethylene glycol molecules [on gold or silver], or b) nitrocellulose [onto any surface]. Nitrocellulose coating is particularly useful as it provides an inert substrate for, for example, protein writing that allows the capture protein to retain its tertiary structure and function. It is possible to write by DPN onto s surface modified by very thin layers of nitrocellulose. The method requires that the tip is first modified by a material that allows protein molecules to interact effectively with it, building up a bulk layer. For gold coated tips the method involves modification using a thiol-polyethylene glycol molecule that is terminated in a carboxylic acid. The tip is then incubated in a buffered solution containing the protein for 30 minutes to several hours. This allows several layers of protein to build up on the surface. DPN writing can then be achieved (using slower tip speeds than would be used conventionally) relying on the weak Van der Waals forces between the nitrocellulose surface and the protein. A full range of DPN pattering can be achieved using this method, including writing onto SE(R)RS surfaces. Signals can be achieved by capture of an analyte molecule. In particular the response of the array is increased significantly by addition of a dye labelled counterpart to the capture protein. With the most efficient detection being achieved if the dye chosen has a electronic absorption maximum that is close to the laser being used for SE(R)RS excitation and the surface plasmon resonance of the SE(R)RS substrate.

3-B: Combination of Reflectivity and SE(R)RS Detection via DPN

The ability of DPN to place capture chemistry into precise locations either in a particular well or surface feature, or even within a single well, allows a new hybrid detection array to be generated.

This type of array is particularly suited to a fast responsive light source such as that provided by piezo controlled micromirrors or dynamic structured illumination. The array would rely on a capture chemistry being placed in an area of high electric field within the feature or well, such as the corners or junctions between facets of the microwells shown in FIG. 1G, H. The addition of a target molecule followed by the addition of a complementary nanoparticle modified counter part has two effects. With precise positioning of the initial capture chemistry, the proximity of the nanoparticle to the surface will have the effect of increasing the local electric field at this point, increasing the SE(R)RS intensity. However, in addition to this, the addition of the nanoparticle will dramatically affect the reflectivity characteristic of the substrate, with very high sensitivity in a similar manner to a surface plasmon resonance detector. DPN pattering of SE(R)RS surfaces allows for the first time the creation of a highly sensitive but also selective combined SPR-SE(R)RS monitor array. Such an array could be monitored using broadband white (or suitable monochromatic light) in order to detect any changes in reflectivity. The substrate surface can also be angle tuned to provide sensitivity at different points in the feature or microwell. Upon the detection of a change in reflectivity at a point in the array, the sensor could then scan the area in higher detail/resolution in order to verify and identify via SE(R)RS the binding event that led to the capture of the large molecule (e.g. a protein) or nanoparticle.

3-C: DPN Can be Used to Create SE(R)RS Substrates:

DPN can be used to create new types of SE(R)RS substrates. This relies on the fact that the strongest local electric field occur on features that that have sub-wavelength dimensions. DPN can be used to place capture chemistry in precise locations to selectively immobilise nanoparticles, nanorods or similar nanomaterials in spatial arrangements such that the local electric field is maximised. DPN can also be used to create patterns of lines, curves and dots that can then be selectively etched and metalized in order to create structures that have surface plasmon resonances at suitable wavelengths for efficient SE(R)RS detection.

Thus, initial DPN writing can be carried out to apply a coating material onto a substrate, which can capture SE(R)RS active material, or it is possible to write passifying materials into areas where it is necessary to 'keep clear' for the purposes of efficient surface plasmon propagation.

In one embodiment the present invention is the combination of dip pin nanolithography to deposit the capture or analyte molecules in dimensions appropriate for optimal SE(R)S signals (i.e. the near field). This is a novel approach method is applicable with many of the structured metal surfaces used to provide the surface enhancement for SE(R)RS which are incorporated herein by reference.[ref 13] For instance a routinely available surface is Klarite® which contains inverted square based pyramids where the dimensions of the pyramid are 1.3 microns. To deposit into an individual well using conventional techniques is almost impossible, however, the use of DPN has allowed the deposition of materials into the individual micron sized wells and subsequent examination by SE(R)RS. Furthermore, DPN allows patterning in dimensions well below the diffraction limit. Detection by quantum dots, molecular fluorescence or other Rayleigh scattering methods is limited in the amount of information that can be embedded into a given spacial area. This is because the optical signature of the reporters in each case are very similar, especially so when using a single wavelength of excitation. Quantum dots are an exception to this in that many can be excited in the blue or UV region of the spectrum, whilst retaining distinct fluorescent shifts that allow for up to 608 different reporters within the range of most detectors. However, excitation in the UV or blue is not suitable as background auto fluorescence can be obtained from many sample matrices, in addition to the potential for sample damage. SERS or SERRS provides an information rich spectrum that can be overlaid with other spectra whilst retaining linearity of the concentration dependant response. Therefore, sample spots can be placed by DPN with spacing's (pitches) smaller than the diffraction limit and yet still allow resolution of the features by Raman mapping or imaging methods. This allows the spectroscopic "tag" and the spatial co-ordinates of the array to be retained in a biosensor array at a resolution many orders of magnitude lower than conventional arrays. In the case of biosensors arrays designed to be read by simple cheap optic techniques and single optical sources, the effective combination of SE(R)RS, DPN and Non-flat plasmon resonant surfaces represents a significant improvement in the art.

In addition, the DPN method allows writing of very thin line features of a molecule (capture or analyte) material in a manner that is not easily achievable by other ligthography methods. This allows even greater throughput to be achieved using suitable optics and mapping methods. For example writing SE(R)RS active line features onto a non flat plasmon resonance surface allows the pattern to be read very quickly and effectively by Raman line mapping methods. The line mapping method works by focussing the excitation source into a line and rastering over the surface, orthogonally to the deposited line on the surface, simultaneously collecting spectra from a large number of points along the line. By placing the DPN generated lines for example horizontally in the array maximum throughput can be achieved (see FIG. 4A below).

In addition this "barcode" type readout removes the need for X AND Y spacial correlation, as the line length in the X axis is very long compared with the Y. Again this allows the throughput of the biosensor array to be maximised. The readout simply begins at the start and rasters through the entire array vertically in X. The line thickness of the features in DPN can be as small as 14 nm. As stated above a major advantage of SERS is that multiple target spectra can be overlaid and read without significant hindrance. Therefore, a simple mapping system with a lateral resolution of approximately 1 µm could potentially read out 30 or more reporters within this spacial region. Current biosensors arrays have feature sizes in the in the range 3-80 µm utilizing only a single reporter in each spot. Combined SE(R)RS-DPN generated arrays can possess many orders of magnitude more information density per unit area. Furthermore the surface plasmons are able to travel a significant distance over the surface in some cases. This allows capture/analyte dot features to be placed in such an arrangement that a strong laser could be directed at a different point (such as a central point—as shown in FIG. 4C) and the optics adapted to read sample points around the central laser delivery point. This allows potential surface burning/damage or localised heating to be reduced (on the spot where the laser is directed) whilst spectra can be read from each array dot point surrounding the sample due to the travelling surface plasmons (see FIG. 4C). Scattering (including SE(R)RS) will be produced at these points remote from the initial laser focus point. DPN allows the placement of samples with such precision (i.e. within the surface plasmon travel distance) to allow this type of array to be generated. This also significantly increases the amount of individual locations that can be read by a single point mapping or readout system.

The combination of DPN, SE(R)RS and structured plasmonic substrates is ideally suited to structured or patterned illumination. More specifically, optical methods exist whereby complex patterns of lines or dots can be obtained using diffractive or similar optics. These lines or dots can be generated with special very small resolutions making them ideal illumination sources for large DPN patterned arrays (see FIGS. 4A-B).

REFERENCES

[1] R. D. Piner, J. Zhu, F. Xu, S. Hong, C. A. Mirkin, *Science* 1999, 283, 661.

[1] L. M. Demers, D. S. Ginger, S-J. Park, Z. Li, S-W Chung, C. A. Mirkin, *Science* 2002, 296, 1836.

[1] L. M. Demers, S-J Park, T. A. Taton, Z. Li, C. A. Mirkin, *Angew. Chem. Int. Ed.* 2001, 40, 3071.

[1] D. S. Ginger, H. Zhang, C. A. Mirkin, *Angew. Chem. Int. Ed.* 2004, 43, 30 (and references therein.)

[1] T. Vo-Dinh, K. Houck, D. L. Stokes, *Anal. Chem.*, 1994, 66(20), 3379-3383.

[1] L. R. Allain, T. Vo-Dinh, *Anal. Chim. Acta.*, 2002 469, 149-154.

[1] Y. C. Cao, R. Jin, C. A. Mirkin, *Science*, 2002, 297(5586), 1536-1540.

[1] R. J. Stokes, A. Macaskill, P. J. Lundahl, K. Faulds, W. E. Smith, D. Graham, *Small* 2007, 3(9), 1593-1601.

[1] R. J. Stokes, A. Macaskill, J. A. Dougan, P. G. Hargreaves, H. M. Stanford, W. E. Smith, K. Faulds, D. Graham, *Chem. Commun.* 2007, 2811-2813.

[1] A. J. Haes, C. L. Haynes, A. D. McFarland, S. Zou, G. C. Schatz, and R. P. Van Duyne, *MRS Bulletin*, 2005, 30, 368.

[1] L. R. Allain, T. Vo-Dinh, *Anal. Chim. Acta.*, 2002, 469, 149-154.

[1] Daniel M. Kuncicky, Brian G. Prevo and Orlin D. Velev, *J. Mater. Chem.*, 2006, 16, 1207.
[1] N. M. B. Perney, J. J. Baumberg, M. E. Zoorob, M. D. B. Charlton, S. Mahnkopf, C. M. Netti, *Optics Express*, 2006 14 (2), 847-857.
[1] (a) D. Graham, C McLaughlin, G. McAnally, J. C. Jones, P. C. White, W. E. Smith, *Chem Commun.* 1998, 1187. (b) G. M. McAnally, C. McLaughlin, R. Brown, D. Robson, K. Faulds, D. R. Tackley, W. E. Smith, D. Graham, *Analyst*, 2002, 127, 838.
[1] R. J. Stokes, A. Ingram, J. Gallagher, D. Armstrong, W. E. Smith, D. Graham, *Chem. Commun.* 2008, 567.
[1] K. Faulds, F. McKenzie, D. Graham, *Angew. Chem. Int. Ed.* 2007, 46, 1829-1831.

The invention claimed is:

1. A method of making a nanoarray for use in SE(R)RS detection comprising:
   patterning a compound on a suitable SE(R)RS active substrate by nanolithographic printing to form a pattern, and;
   providing a coating or intermediate layer between the compound being bound and the SE(R)RS active surface, wherein the coating is a layer of nitrocellulose.

2. The method according to claim 1 wherein the nanolithographic printing is carried out by dip pen nanolithographic printing.

3. The method according to claim 1 wherein the SE(R)RS substrate is selected from the group consisting of surfaces roughened by the oxidation-reduction cycle (ORC), island films, colloidal nanoparticles and surface-confined nanostructures.

4. The method according to claim 1 wherein the SE(R)RS substrate is a patterned silicon surface coated in gold.

5. The method according to claim 2 wherein the patterned compound forms features which are closer together than the diffraction limit.

6. The method of claim 1 wherein the pattern of the compound has features which are less than 25 nm and can be less than 25 nm apart.

7. A method of detecting a SE(R)RS signal comprising:
   a) providing a microarray prepared in accordance with claim 1;
   b) adding a second compound to said microarray in order to allow any complex formation to occur between the first patterned compound and the second compound; and
   c) detecting any complex formed between the first and second compounds by use of a suitable SE(R)RS detection technique.

8. The method according to claim 7 wherein the detection of complex formation is carried out using a laser spot focus point which is not positioned directly over the formed complex or first patterned compound.

9. The method according to claim 7 wherein the first or second compound comprises a SE(R)RS detectable chromophore or the first and second compounds when complexed comprise a SE(R)RS detectable chromophore.

10. The method according to claim 7 wherein prior to detecting any complex by way of a suitable SE(R)RS technique, the array is initially scanned using a reflectivity scan in order to identify areas on the microarray which display altered reflectivity.

11. The method according to claim 7 wherein the suitable SE(R)RS technique employs wavelength selective mirrors, holographic optical elements for scattered light detection or fibre-optic waveguides.

12. The method according to claim 7 wherein the intensity of a SE(R)RS signal is measured using a charge coupled device (CCD), a silicon photodiode, or photomultiplier tubes arranged either singly or in series for cascade amplification of the signal.

13. The method according to claim 7 wherein the SE(R)RS detection technique includes a data processor for analysis of a SE(R)RS signal.

\* \* \* \* \*